United States Patent [19]

Gindler et al.

[11] Patent Number: 4,474,888

[45] Date of Patent: * Oct. 2, 1984

[54] DETERMINATION OF UREA

[75] Inventors: E. Melvin Gindler, Union City; Olga Daskalakis, Burlingame, both of Calif.

[73] Assignee: Sherwood Medical Company, St. Louis, Mo.

[*] Notice: The portion of the term of this patent subsequent to Nov. 2, 1999 has been disclaimed.

[21] Appl. No.: 437,222

[22] Filed: Oct. 28, 1982

Related U.S. Application Data

[63] Continuation-in-part of Ser. No. 292,959, Aug. 14, 1981, Pat. No. 4,357,144.

[51] Int. Cl.³ ............................................. G01N 33/62
[52] U.S. Cl. ...................................... 436/108; 422/61
[58] Field of Search ........................... 436/108; 422/61

[56] References Cited

U.S. PATENT DOCUMENTS

| | | |
|---|---|---|
| 3,890,099 | 6/1975 | Jung . |
| 4,074,972 | 2/1978 | Denney . |
| 4,105,408 | 8/1978 | Denney . |
| 4,131,425 | 12/1978 | Denney . |
| 4,131,429 | 12/1978 | Denney . |
| 4,131,430 | 12/1978 | Denney . |
| 4,215,995 | 8/1980 | Turk . |
| 4,239,649 | 12/1980 | Gindler . |
| 4,273,556 | 6/1981 | Gindler . |
| 4,357,144 | 11/1982 | Gindler . |

OTHER PUBLICATIONS

Chemical Abstracts, 90: 199783u (1979).
D. Jung et al., Clin, Chem., 21 (8), 1136–1140 (1975).

Primary Examiner—Sidney Marantz
Attorney, Agent, or Firm—Stanley N. Garber; Gregory E. Upchurch; William R. O'Meara

[57] ABSTRACT

A colorimetric urea determination method, reagent, and reagent kit useful in end point and kinetic urea determination is disclosed. Urea in a liquid sample reacts with o-phthalaldehyde and a chromogenic compound in the presence of a linear long hydrocarbon chain amidobetaine to produce an intensely colored reaction product, the concentration of which is linearly related to the urea concentration in the sample.

17 Claims, No Drawings

DETERMINATION OF UREA

CROSS-REFERENCE TO RELATED APPLICATION

This is a continuation-in-part of commonly assigned application Ser. No. 292,959 filed Aug. 14, 1981 entitled "Colorimetric Urea Determination In Presence of Long Hydrocarbon Chain Amidobetaine" now U.S. Pat. No. 4,357,144 issued Nov. 2, 1982.

BACKGROUND OF THE INVENTION

1. Field of the Invention

This invention relates to urea assay methodology and, more particularly, this invention relates to a colorimetric urea determination method, reagent and reagent kit useful in end point and kinetic urea determination methods.

2. Description of the Prior Art

Various methods of urea demonstration and determination utilize a reaction between urea, o-phthalaldehyde and a chromogenic compound, in which an intensely colored reaction product is produced. For example, Gindler U.S. Pat. No. 4,273,556, the disclosure of which is hereby incorporated by reference, describes a method of urea demonstration and determination in which urea reacts with o-phthalaldehyde and chromotropic acid or one of its salts.

According to the prior Gindler patent, o-phthalaldehyde reacts in an acidic medium with urea present in a liquid sample to form a substantially colorless isoindoline derivative, which in turn reacts with chromotropic acid, or one of its salts, to produce an intensely colored substance of unknown structure whose concentration is linearly related to urea concentration.

Prior o-phthalaldehyde based urea demonstration and determination systems using chromogenic compounds other than chromotropic acid are disclosed in Jung U.S. Pat. No. 3,890,099 and Denney U.S. Pat. Nos. 4,074,972, 4,105,408, 4,131,425 4,131,429 and 4,131,430. The disclosures of each of the foregoing Jung and Denney patents are hereby incorporated by reference.

It has been found in practice that, while the reaction systems described in the prior Gindler, Jung and Denney patents exhibit excellent precision in an end point urea determination, the precision of the kinetic method of analysis, in which absorbance readings of the reaction vessel and a calibrator are taken at two time points and the difference between the absorbances compared, is inferior to the precision of the end point method.

Further, when an aqueous calibrator is used in serum assays, an empirical conversion factor between serum absorbance and serum urea concentrations is required.

SUMMARY OF THE INVENTION

It is an object of the invention to overcome one or more of the problems described above.

According to the present invention, the colorimetric reaction between urea, o-phthalaldehyde, and a chromogenic compound is carried out in the presence of a long hydrocarbon chain amidobetaine. Preferred amidobetaines have the following structures:

$$R-\underset{\underset{}{||}}{C}-\underset{\underset{}{|}}{N}-(CH_2)_3-\underset{\underset{CH_3}{|}}{N^\oplus}-CH_2-\underset{\underset{}{||}}{C}-O^\ominus$$
$$\phantom{R-}O\phantom{-}H\phantom{-(CH_2)_3-}CH_3\phantom{-CH_2-}O$$

-continued $$R-\underset{\underset{}{||}}{C}-\underset{\underset{}{|}}{N}-(CH_2)_3-\underset{\underset{CH_3}{|}}{N^\oplus}-CH_2-\underset{\underset{H}{|}}{\overset{\overset{CH_3}{|}}{C}}-CH_2-SO_2-O^\ominus$$

wherein R represents a straight chain coconut oil residue having between about 10 and 20 carbon atoms.

The amidobetaine may be used as the only surfactant in the system, and effectively prevents protein precipitation at low pH. Precision of the reaction system when used in a kinetic urea determination method is enhanced, and no empirical conversion factor between serum urea and absorbance is necessary when an aqueous calibrator is used.

Other objects and advantages of the invention will be apparent from the following detailed description taken in conjunction with the appended claims.

DETAILED DESCRIPTION OF THE INVENTION

According to the present invention, o-phthalaldehyde reacts in an acidic medium with urea present in a liquid sample to form a substantially colorless isoindoline derivative concentrate, according to the following:

o-phthalaldehyde + Urea →

(intermediate A)

(intermediate B)

A chromogen reacts with either intermediate (form A or B) in the presence of a long chain amidobetaine to produce an intensely colored substance of unknown structure whose concentration is linearly related to urea concentration, and which follows Beer's law over a wide range of urea concentrations.

Preferred amidobetaines are the carboxy- and sulfobetaines marketed under the trademark LONZAINE® C and LONZAINE® CS, respectively, by the Swiss firm Lonza. The preferred betaines have the following structure:

LONZAINE ® C:

$$R-\underset{\underset{}{||}}{C}-\underset{\underset{}{|}}{N}-(CH_2)_3-\underset{\underset{CH_3}{|}}{N^\oplus}-CH_2-\underset{\underset{}{||}}{C}-O^\ominus$$

-continued

LONZAINE ® CS:

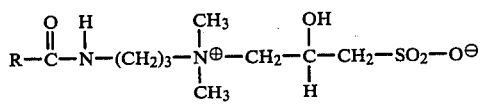

wherein R represents a straight chain coconut oil residue having between about 10 and 14 carbon atoms in the chain.

LONZAINE ® C and CS are commercially available as solutions containing 30% and 50% active ingredient, respectively, at pH ranges of about 4.5–5.5 and 7.0–8.5, respectively.

The prior art discloses many chromogenic compounds suitable for use in o-phthalaldehyde based urea detection systems, as set forth below. These compounds are suitable for use in this invention. The following identification of chromogens is not intended to be exhaustive, as those skilled in the art can readily empirically determine the utility of a given chromogen in the disclosed reaction system.

More specifically, the chromogenic compounds disclosed in the Gindler, Jung and Denney patents identified above and incorporated herein by reference are suitable for use in this invention.

Chromotropic acid (4,5-dihydroxynaphthalene-2,7-disulfonic acid), as disclosed in Gindler U.S. Pat. No. 4,273,556, has the following structure:

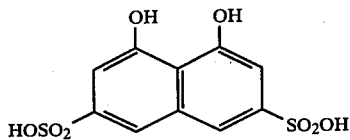

Chromotropic acid is preferably used in salt form. The disodium salt of 4,5-dihydroxynaphthalene-2,7-disulfonic acid dihydrate is especially preferred.

The chromogenic compound of Jung U.S. Pat. No. 3,890,099 is N-(1-napthyl) ethylene-diamine dihydrochloride.

The series of Denney patents, identified above, disclose six major classes of compounds which function as chromogenic compounds in the urea/o-phthalaldehyde reaction system. They are as follows:

A. 1,3 or 1,3,5 di- or tri-substituted hydroxy or methoxy benzene compounds, which have the following general structure:

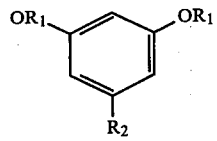

where $R_1$=—H or —CH$_3$ and where $R_2$=—H, or —OH, or —OCH$_3$.

Examples of this class are:
  a. 1,3-dihydroxybenzene
  b. 1,3,5-trihydroxybenzene
  c. 1,3-dimethoxybenzene B. 1, or 1,3 mono- or di-substituted hydroxy or methoxy naphthalene compounds which have the following general formula:

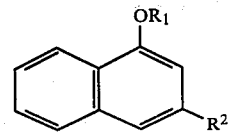

Examples of this class of compounds are:
  a. (1,3-dihydroxynaphthalene)
  b. (1-hydroxynaphthalene) C. 4 or 4,6 substituted 2-aminopyrimidines, where the substituting group is an electron withdrawing group possessing the following general structure:

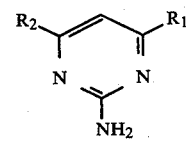

where $R_1$=—H, or —OH, or —OCH$_3$ and where $R_2$ is —OH or —OCH$_3$.

Examples of this class of compounds are:
  a. 4,6dihydroxy-2-aminopyrimidine
  b. 4-methoxy-2-aminopyrimidine D. Those compounds which have the following general structure:

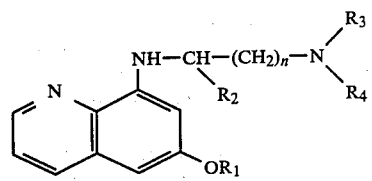

where $R_1$=—H or —CH$_3$ and where $R_2$=—CH$_3$ or —C$_2$H$_5$ or —H and where $R_3$ and $R_4$=—H or —CH$_3$ and where n=1,2, or 3.

An example of this general class of compounds is:
  a. 8-(4-amino-1-methylbutylamino)-6-methoxyquinoline. E. Those compounds which have the following general structure:

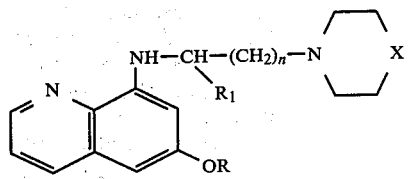

where
R=—H, or —CH$_3$
$R_1$=—CH$_3$, or —CH$_2$CH$_3$ or —H or —CH$_2$CH$_2$—CH$_3$
X=O or C
n=1, 2, or 3.

An example of this class is:
  a. 8-(2-N-morpholinoethylamino)-6-methoxyquinoline. F. Those compounds which have the following general structure:

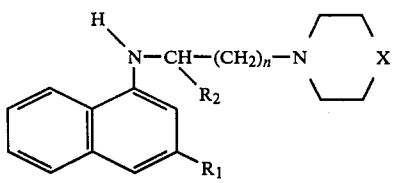

wherein $R_1 =$ —H, —OCH, or —OH and where $R_2 =$ —H, —CH$_3$ or —C$_2$H$_5$ where X=O or C and where n=1, 2 or 3.

An example of this class of compounds is:

a. 2-N-morpholinoethyl-1-naphthylamine.

In the practice of the invention, a urea-containing liquid sample is mixed with a working reagent comprising an acidic solution of o-phthalaldehyde, the chromogenic compound, and the amidobetaine. The reagent preferably contains sulfuric acid. Only about 2 mL of working reagent is required for each 10 μL of sample in the end point procedure and 2 mL of working reagent for each 50 μL of sample in the kinetic procedure.

The working reagent is preferably prepared by mixing a first aqueous reagent solution comprising o-phthalaldehyde and sulfuric acid with a second aqueous reagent solution comprising the chromogenic compound, the amidobetaine, and sulfuric acid.

If desired, a small amount of ethylene glycol can be included in the chromogenic compound solution to enhance stability.

The Gindler, Jung and Denney patents disclose specific working reagent compositions which may be used in this invention if the amidobetaine is also present in the reagent.

Upon mixing of the urea-containing liquid sample with the working reagent, the o-phthalaldehyde and urea react to form the isoindoline derivative intermediate, as described above, which in turn reacts with the chromogenic compound component to produce an intensely colored reaction product the concentration of which is linearly related to the urea concentration in the sample, and which follows Beer's law over a wide range of urea concentrations. The concentration of the colored substance is readily determinable by standard spectrophotometric techniques.

The presence of the amidobetaine enhances precision, prevents protein precipitation, enhances the flow properties of the reagent system, and eliminates the need for an empirical conversion factor between serum absorbance and urea concentration when an aqueous calibrator is used.

The color-forming reaction is conveniently carried out at between about 25° C. and 37° C., preferably at 37° C. The method and reagent of the invention is suitable for end point, continuous flow, and kinetic urea measurement. Due to the presence of the amidobetaine, the reagent of the invention is particularly suitable for use in analytic having flow-through cuvettes, and will not attack polymeric cuvette materials, even after long exposure.

The reagent is suitable for use in virtually any colorimetric instrument having programmable incubation facilities, or in equipment having constant temperature equipment, such as a constant temperature bath or block.

In the case of the chromotropic acid reagent, maximum absorbance occurs at between about 445–455 nm at 37° C. The color-forming reaction in the end point procedure is rapid; after a reaction time of less than about 20 minutes, the colored reaction product follows Beer's law over the range of at least 0–80 mg urea nitrogen/dl. The total reaction time in the manual kinetic procedure need not exceed 2.5 minutes.

The wavelength of maximum absorbance may vary depending upon the particular chromogenic compound employed, but in all cases is readily empirically determinable. The Jung and Denney patents disclose wavelengths of maximum absorbance for systems using various chromogenic compounds.

The invention is useful in the analysis of urea in any type of sample, including substantially colorless body fluids, such as urine, spinal fluid, blood serum and blood plasma, or in naturally colored body fluids such as whole blood, for example. To analyze naturally colored fluids, an absorbance reading should be taken immediately before the reaction starts, and 20 minutes after initiation of the reaction. The difference in absorbance readings corresponds to the concentration of the colored reaction product, as determined by comparison with an aqueous or serum calibrator.

The reagent of the invention is highly soluble in aqueous solutions under a wide variety of conditions.

Use of the reagent system of the invention enhances the precision of the well-known kinetic method of determination, as compared with the prior o-phthalaldehyde based urea determination systems.

In the kinetic urea determination method, the reagents are mixed with a urea-containing liquid sample, and the absorbance of the reaction mixture at the end of a first time period (e.g. 30 seconds) and the absorbance at the end of a second time period (e.g. 90 or 120 seconds) after mixing are taken. The difference between these absorbances is then compared directly with a calibration graph obtained using aqueous calibrator solutions. No empirical conversion factor between serum and aqueous calibrator absorbances is required. In the manual kinetic procedure, a 60-second delay is used at room temperature following the mixture of 50 μL of sample and 2.00 mL working reagent before following the color development over 90 or 120 minutes at 37° C.

Both of the specific amidobetaines disclosed herein provide improved results over prior urea determination systems, but the sulfoamidobetaine (e.g. LONZAINE ® CS) has proven to be more sensitive than the carboxyamidobetaine (LONZAINE ® C).

The ratios of reagents described in the Examples, below, may be varied, but the reaction rate decreases with decreasing o-phthalaldehyde concentrations. Also, the ratios of stock reagents may be varied.

The amidobetaines effectively prevent protein precipitation, and may be used as the only surfactant in the system.

The reagents of the invention are adequately stable in aqueous acidic solutions. The chromogenic compound component may be packaged in an aqueous acid solution, which preferably includes and amidobetaine, for addition to separately packaged o-phthalaldehyde solution to form the working reagent. Thus, only two solutions are required.

The working reagent is adequately stable, and need not be prepared immediately before use, but may be stored for a period of at least several days at room temperature.

EXAMPLES

The use of the method and reagents of the invention is illustrated by reference to the following detailed examples. It should be understood, however, that the invention is not to be limited to the details of the examples, which are intended to be illustrative only.

Example 1—Preparation of Working Reagent of the Invention

A. O-phthalaldehyde Reagent Solution

An o-phthalaldehyde solution is prepared by mixing 2.08 gm o-phthalaldehyde and 85.33 mL concentration (18M) sulfuric acid. The solution volume is brought to 1 liter by addition of deionized water.

B. Chromogenic Compound Solution I

A quantity of deionized water is mixed with 48.0 gm of 4,5-dihydroxynaphthalene-2,7-disulfonic acid disodium salt, dihydrate (98%), 540 mL LONZAINE® CS, 280 mL ethylene glycol, and 2.5 mL concentrated (18 M) sulfuric acid. The use of ethylene glycol is optional, and enhances stability.

The solution volume is brought to 1 liter by addition of deionized water.

C. Chromogenic Compound Solution II

A quantity of deionized water is mixed with 48 gm of 4,5-dihydroxynaphthalene-2,7-disulfonic acid disodium salt, dihydrate (98%), 748 ml LONZAINE® C, and 4.0 ml concentrated (18 M) sulfuric acid.

The solution volume is brough to 1 liter by addition of deionized water.

D. Working Reagent

Two working reagents are prepared by mixing 15 volumes of the o-phthalaldehyde reagent solution (Example 1(A)) with 1 volume of either of the chromogenic compound solutions I or II (Examples 2(B) and 2(C)), after filtering each of the solutions through Whatman No. 54 filter paper. The working reagents are referred to herein as working reagents I and II, respectively.

Example 2—Preparation of Reference Working Reagent (U.S. Pat. No. 4,273,556)

A. O-phthalaldehyde Reagent Solution

An o-phthalaldehyde solution is prepared by mixing 3.90 gm o-phthalaldehyde and 160 mL concentrated (18 M) sulfuric acid. The solution volume is brought to 1 liter by addition of deionized water.

B. Chromogenic Compound Solution

A quantity of deionized water is mixed with the following:
8.5 gm 4,5-dihydroxynaphthalene-2,7-disulfonic acid
  (Aldrich, disodium salt,
  dihydrate, 98%)
50 mL ethylene glycol
8.5 mL concentrated sulfuric acid (18 M)
25 gm Armak ETHOMEEN® C/25
22.5 gm BASF Wyandotte PLURONIC® 25R8
34 gm BASF Wyandotte TETRONIC® 707
25 gm boric acid The solution volume is brought to 1 liter by addition of deionized water.

ETHOMEEN® C/25 comprises cocoamine having 15 ethylene oxide units per molecule, and effectively prevents protein precipitation. The use of PLURONIC® 25R8 and TETRONIC® 707 eliminates turbidity.

C. Working Reagent

Equal volumes of the o-phthalaldehyde solution (Example 2(a)) and chromogenic compound solution (Example 2(B)) are mixed after filtration of each solution through Whatman No. 54 filter paper.

Example 3—Kinetic Urea Determination Using Reference Working Reagent (U.S. Pat. No. 4,273,556)

Kinetic urea nitrogen determination was carried out on a series of samples of human sera, using the following procedure:

2.00 mL of the reagent of Example 2(C) was added to 50 μL of each sample. Each sample was incubated for 50 seconds at room temperature and placed in a Gilford Stasar III thermocuvet at 36.94° C. and the absorbance at 450 nm was recorded at intervals of 30 seconds and 120 seconds.

Each sample had previously been analyzed for urea nitrogen concentration by the SMAC® multiple Auto Analyzer® method, to provide "given" urea nitrogen values (mg/dL). "Found" urea nitrogen values, F, were calculated by direct comparison of the difference in absorbance between 120 and 30 seconds with an aqueous calibrator.

The "found" values were uniformly lower than the given values. Therefore, the use of an empirical conversion factor, as follows, was necessary.

The serum urea nitrogen concentration was found to be equal to 44 W/D (mg/dL) where W equals the absorbance change for serum between 30 and 120 seconds and D equals the absorbance change for a 40 mg/dL aqueous calibrator between 30 and 120 seconds. In this case, D=0.2605 and 44/D=168.8.

After carrying out the foregoing analysis on 50 serum specimens, a least squares analysis indicated that, with the use of the empirical conversion factor given above, the correlation coefficient between given values and values found using the empirical conversion factor was 0.9986.

Example 4—Kinetic Urea Determination Using Working Reagents I and II of Example 1

Kinetic urea determination was performed on two series of human sera using working reagents I and II of Example 1(D), and following the procedure of Example 3, except that differential absorbance readings were taken at 30 and 90 seconds, rather than at 30 and 120 seconds.

It was found in each case that the "found" urea nitrogen values F corresponded with the "given" values G determined independently by SMAC® analysis, and no empirical conversion factor between serum absorbance and serum urea nitrogen concentration was necessary.

In each case, statistical analyses (Student-t Test, Wilcoxon Signed Rank Test, Sign Test) indicated that an upward bias of about 1 mg/dL existed between the method of the invention and the "given" (SMAC®) values. No significant difference between the ([Found Value]−1 mg urea nitrogen/dL) and the corresponding given values existed.

The correlation coefficient between given values and found values (without the use of an empirical conversion factor) was 0.997.

While the foregoing Examples illustrate the practice of the invention with reference to the use of chromotropic acid as the chromogenic compound, it is to be understood that the invention can be readily carried out using the chromogenic compounds and associated procedures disclosed in the Examples of the Jung and Denney patents identified above, using proportions of amidobetaines which are roughly equivalent to those disclosed herein, although proportions may be varied within a wide range. Selection of proportions of amidobetaines is readily empirically accomplished by one skilled in the art.

The foregoing detailed description is given for clearness of understanding only and no unnecessary limitations are to be understood therefrom, as modifications will be obvious to those skilled in the art.

We claim:

1. A method of demonstrating the presence of urea in a liquid sample, said method comprising the step of mixing said sample with a reagent comprising o-phthalaldehyde, a chromogenic compound, and a long hydrocarbon chain amidobetaine to produce a colored reaction product.

2. The method of claim 1 wherein said betaine is a sulfo- or carboxy-betaine.

3. The method of claim 2 wherein said betaine has either of the following structures:

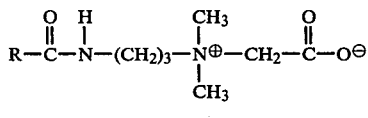

or

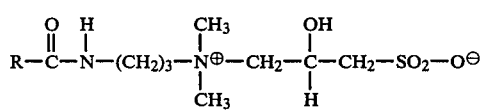

where R is a straight chain coconut oil residue having between about 10 and 14 carbon atoms in said chain.

4. A method of demonstrating the presence of urea in a sample of human body fluid comprising the step of mixing said sample with o-phthalaldehyde and a chromogenic compound under slightly acidic conditions in the presence of an amidobetaine having either of the following structures:

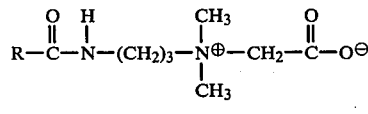

or

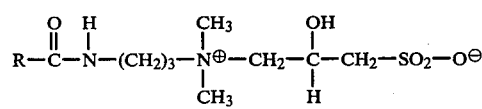

where R is a straight chain coconut oil residue having between about 10 and 14 carbon atoms in said chain, to produce a colored reaction product.

5. A method of determining the urea concentration in a liquid sample comprising the steps of:
   (a) adding o-phthalaldehyde, a chromogenic compound and a long hydrocarbon chain amidobetaine to said liquid sample;
   (b) maintaining said sample at a temperature at which said chromogenic compound, said o-phthalaldehyde and said urea in said sample react to produce a colored reaction product;
   (c) obtaining a colorimetric absorbance reading for said sample; and
   (d) comparing said absorbance reading with calibration means.

6. The method of claim 5 wherein said amidobetaine has either of the following structures:

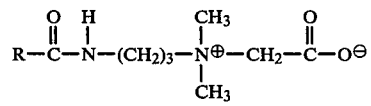

or

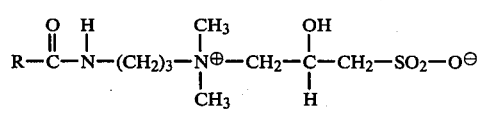

where R is a straight chain coconut oil residue having between about 10 and 14 carbon atoms in said chain.

7. In a method of determining the urea concentration in a liquid sample comprising the steps of mixing said sample with o-phthalaldehyde and a chromogenic compound under slightly acidic conditions to form a colored reaction product, obtaining a colorimetric absorbance reading of said sample and comparing said absorbance reading with calibration means, the improvement wherein said colored reaction product is formed in the presence of a long hydrocarbon chain amidobetaine.

8. The method of claim 7 wherein said amidobetaine has either of the following structures:

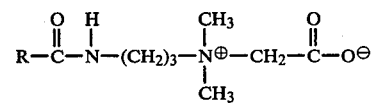

or

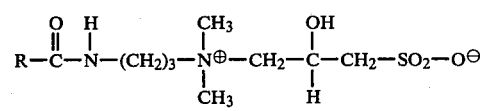

where R is a straight chain coconut oil residue having between about 10 and 14 carbon atoms in said chain.

9. A method of determining the urea concentration of a liquid sample, said method comprising the steps of:
   (a) adding said sample to a sample container;
   (b) adding equal amounts of a reagent comprising a solution of o-phthalaldehyde, a chromogenic compound and a long hydrocarbon chain amidobetaine to said sample container and a blank container;
   (c) maintaining the contents of each said container at a temperature at which said chromogenic compound, said o-phthalaldehyde and said urea in said sample react to produce a colored reaction product;
   (d) obtaining first colorimetric absorbance readings for each of said blank and sample containers at the end of a first time period;
   (e) obtaining second colorimetric absorbance readings for each of said blank and sample containers at the end of a second time period;

(f) computing the difference between said first and second absorbance readings for each of said dample and blank containers; and, (g) comparing said differences with calibration means.

10. The method of claim 9 wherein said amidobetaine is selected from the group consisting of betaines having the following structures:

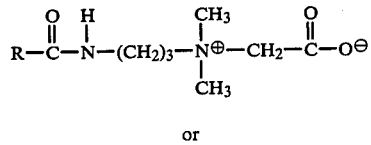

or

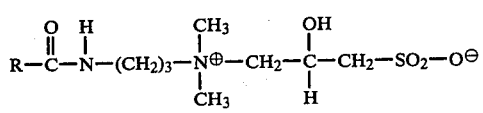

where R is a straight chain coconut oil residue having between about 10 and 14 carbon atoms in said chain.

11. The method of claim 1, 4, 6, 7 or 9 wherein said chromogenic compound is selected from the group consisting of:

(a) N-(1-napthyl)ethylene-diamine dihydrochloride; and compounds of the following general structures:

(b)

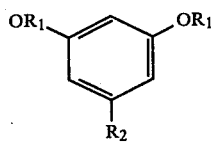

where $R_1$ =—H or —CH$_3$ and
where $R_2$ =—H, or —OH, or —OCH$_3$ (c)

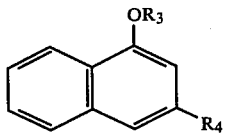

where $R_3$ =—H or —OH$_3$ and
where $R_4$ =—H, or —OCH$_3$, or —OH.

(d)

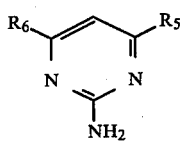

where $R_5$ is —H, or —OH, or —OCH$_3$ and
where $R_6$ is —OH or —OCH$_3$ (e)

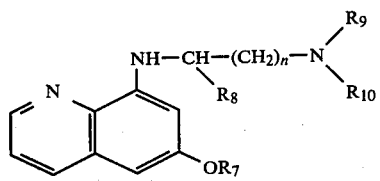

where $R_7$ =—H or —CH$_3$ or where $R_8$ =—CH$_3$ or —C$_2$H$_5$ or —H and
where $R_9$ and $R_{10}$ —H or —CH$_3$ and
where n=1, 2, or 3

(f)

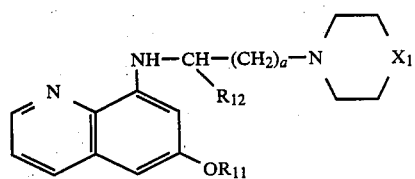

where $R_{11}$ =—H, or —CH$_3$
$R_{12}$ =—CH$_3$, or —CH$_2$CH$_3$ or —H or —CH$_2$CH$_2$—CH$_3$
$X_1$ =O or C
a=1,2 or 3, and (g)

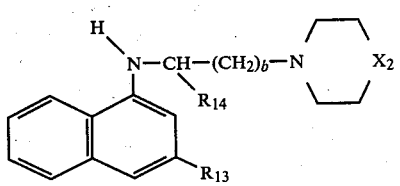

where $R_{13}$ =—H, —OCH, or —OH and
where $R_{14}$ =—H, —CH$_3$ or —C$_2$H$_5$ and
where b=1, 2 or 3.

12. A reagent for colorimetric urea determination consisting essentially of a solution of (a) o-phthalaldehyde, (b) a chromogenic compound, and (c) a long hydrocarbon chain amidobetaine.

13. A reagent for colorimetric urea determination consisting essentially of an acidic solution of (a) o-phthalaldehyde, (b) a chromogenic compound, and (c) a long hydrocarbon chain amidobetaine selected from the group consisting of compounds of the formula

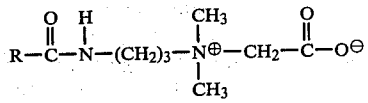

or

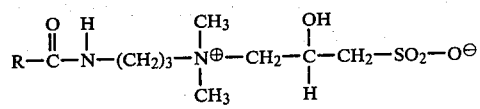

where R is a straight chain coconut oil residue having between about 10 and 14 carbon atoms in said chain.

14. The reagent of claim 12 or 13 wherein said chromogenic compound is selected from the class consisting of:

(a) N-(1-napthyl)ethylene-diamine dihydrochloride; and compounds of the following general structures:

(b)

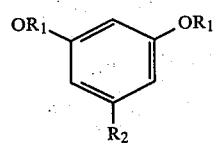

where $R_1$ = —H or —CH$_3$ and
where $R_2$ = —H, or —OH, or —OCH$_3$

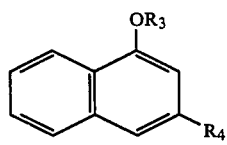
(c)

where $R_3$ = —H or —CH$_3$ and
where $R_4$ = —H, or —OCH$_3$, or —OH.

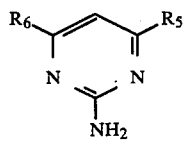
(d)

where $R_5$ is —H, or —OH, or —OCH$_3$ and
where $R_6$ is —OH or —OCH$_3$

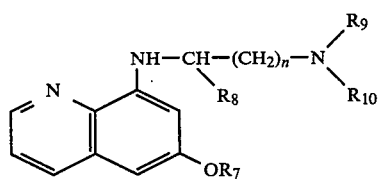
(e)

where $R_7$ = —H or —CH$_3$ or
where $R_8$ = —CH$_3$ or =C$_2$H$_5$ or —H and
where $R_9$ and $R_{10}$ = —H or —CH$_3$ and
where n = 1, 2, or 3

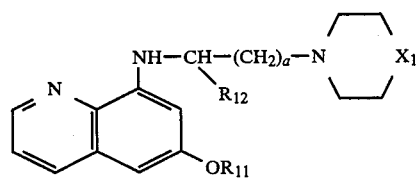
(f)

where $R_{11}$ = —H, or —CH$_3$
$R_{12}$ = —CH$_3$, or —CH$_2$CH$_3$ or —H or —CH$_2$CH$_2$—CH$_3$
$X_1$ = O or C
a = 1, 2 or 3, and

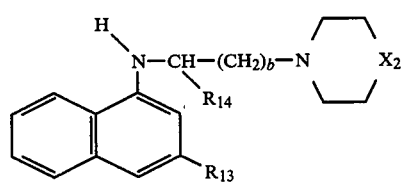
(g)

where $R_{13}$ = —H, —OCH, or —OH and
where $R_{14}$ = —H, —CH$_3$ or —C$_2$H$_5$ and
where $X_2$ = O or C and
where b = 1, 2 or 3.

15. A reagent kit for colorimetric determination of urea, said reagent kit consisting of a package containing a first container containing a first solution comprising a colorimetric amount of a chromogen and a second container containing a second solution comprising a colorimetric amount of o-phthalaldehyde, one of said first and second solutions further comprising a long hydrocarbon chain amidobetaine.

16. The reagent kit of claim 15 wherein said amidobetaine is selected from the group consisting of compounds of the formula

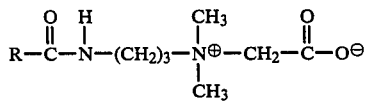

or

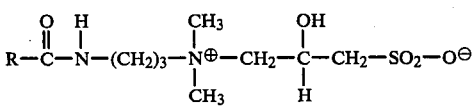

where R is a straight chain coconut oil residue having between about 10 and 14 carbon atoms in said chain.

17. The kit of claim 15 wherein said chromogenic compound is selected from the class consisting of:
(a) N-(1-napthyl)ethylene-diamine dihydrochloride; and compounds of the following general structures:

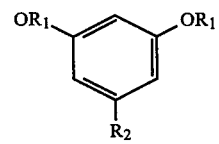
(b)

where $R_1$ = —H or —CH$_3$ and
where $R_2$ = —H, or —OH, or —OCH$_3$

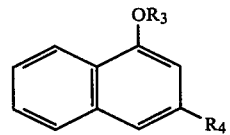
(c)

where $R_3$ = —H or —CH$_3$ and
where $R_4$ = —H, or —OCH$_3$, or —OH.

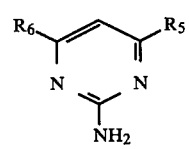
(d)

where $R_5$ is —H, or —OH, or —OCH$_3$ and
where $R_6$ is —OH or —OCH$_3$

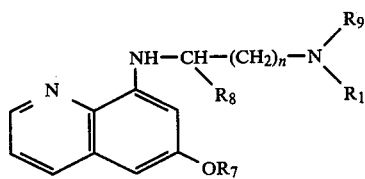
(e)

where $R_7$ = —H or —CH$_3$ or
where $R_8$ = —CH$_3$ or —C$_2$H$_5$ or —H and
where $R_9$ and $R_{10}$ = —H or —CH$_3$ and
where n = 1, 2, or 3

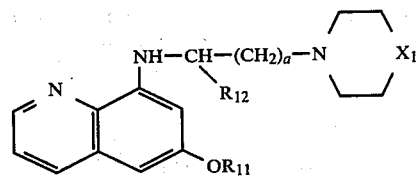 (f)
where $R_{11}$ = —H, or —CH$_3$
$R_{12}$ = —CH$_3$, or —CH$_2$CH$_3$ or —H or —CH$_2$CH$_2$—CH$_3$
$X_1$ = O or C
$a$ = 1, 2 or 3, and
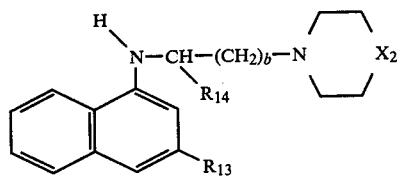 (g)
where $R_{13}$ = —H, —OCH, or —OH and
where $R_{14}$ = —H, —CH$_3$ or —C$_2$H$_5$ and
where $X_2$ = O or C and
where $b$ = 1, 2 or 3.
* * * * *